United States Patent [19]

Lewis et al.

[11] Patent Number: 4,730,074
[45] Date of Patent: Mar. 8, 1988

[54] VAPOR PHASE ALCOHOLYSIS OF AMINOSILANES AND CARBAMATOSILANES

[75] Inventors: Kenrick M. Lewis, Rego Park, N.Y.; Frank D. Mendicino, Marietta, Ohio; Nan S. Chu, Hartsdale, N.Y.

[73] Assignee: Union Carbide Corporation, Danbury, Conn.

[21] Appl. No.: 948,036

[22] Filed: Dec. 31, 1986

[51] Int. Cl.$^4$ .............................................. C07F 7/18
[52] U.S. Cl. ................................................... 556/470
[58] Field of Search ........................................ 556/470

[56] References Cited

U.S. PATENT DOCUMENTS 4,395,564 7/1983 Kanner et al. ...................... 556/470

Primary Examiner—Paul F. Shaver
Attorney, Agent, or Firm—S. H. Flynn

[57] ABSTRACT

A vapor phase process for the synthesis of alkoxysilanes of the general formula $HSi(OR''')_x(R'')_{3-x}$ which comprises reacting (a) a silane of the general formula $$HSi(NRR')_x(R'')_{3-x}$$

wherein R, R' and R'' are individually hydrogen or an aryl or alkyl group optionally containing unsaturation, each having from one to eight carbon atoms inclusive, and where R' may also be an alkoxy or carbamato group and where x has a value of from one to three; with (b) an alcohol of the general formula $$R'''OH$$

wherein R''' is an aryl group, or an alkyl group optionally containing unsaturation, each having from one to twenty carbon atoms inclusive and optionally substituted said reaction taking place in the presence of (c) a catalyst in which both the silane and the alcohol are present in gaseous form in a stoichiometric ratio of 0.4 to 1.05 moles of alcohol per mole of silicon-nitrogen bonds and where said catalyst is present in an amount from 0.01 to 10 mole percent of the silicon-nitrogen bonds.

26 Claims, No Drawings

VAPOR PHASE ALCOHOLYSIS OF AMINOSILANES AND CARBAMATOSILANES

BACKGROUND OF THE INVENTION

1. Field of the Invention

The present invention relates to a process for the synthesis of alkoxysilanes, particularly trialkoxysilanes such as trimethoxysilane. More particularly, the present invention relates to a vapor-phase process for reacting aminosilanes, alkoxyaminosilanes, aminocarbamatosilanes, alkoxycarbamatosilanes and alkoxyaminocarbamatosilanes with alcohols in the presence of a catalyst and under the appropriate reaction conditions to produce these trialkoxysilanes.

2. Prior Art

Trialkoxysilanes are used extensively in hydrosilation reactions, especially those directed at the manufacture of silane coupling agents. See, for example, Plueddemann, Silane Coupling Agents, Chapter 2, Plenum Press, New York 1982.

The most common reaction for the synthesis of these trialkoxysilanes is an alcoholysis reaction using trihalosilanes as a starting reactant. See R. J. H. Voorhoeve, Organohalosilanes: Precursors of Silicones, pp. 301–306, Elsevier, New York, 1967. This reaction is as follows:

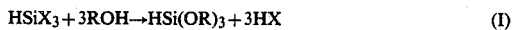

$$HSiX_3 + 3ROH \rightarrow HSi(OR)_3 + 3HX \quad (I)$$

where X is halogen, R is a monovalent alkyl radical containing up to about twenty carbon atoms and $HSi(OR)_3$ represents a trialkoxysilane such as trimethoxysilane.

A major deficiency of this prior art process is that the Si-H bond in the trialkoxysilane is destroyed and replaced with an SiOR bond in a side reaction to produce tetraalkoxysilanes, $Si(OR)_4$, and mixed alkoxyhalosilanes, $X_aSi(OR)_{4-a}$ where a is an integer greater than or equal to one and less than or equal to three. While some tetraalkoxysilanes, e.g., tetraethoxysilane may have some commercial utility, most are undesirable by-products. In addition, tetramethoxysilane is known to be quite toxic, Chemical Engineering News, Vol. 24, p. 1690 (1946), and its formation should be avoided.

As seen in reaction (I), this side reaction is very difficult to avoid because the HX molecule catalyzes the reaction of alcohol, ROH, with the Si-H bond on the trialkoxysilane. Because 3 moles of hydrogen halide are produced per mole of trialkoxysilane made, and because there is a stoichiometric excess of alcohol in the conventional batchwise liquid phase process, this reaction is particularly difficult to avoid.

Further, if a more sterically hindered alcohol is used in reaction (I) such as tert-butyl alcohol for example, the hydrogen halide reacts with the alcohol to give tert-butyl halides and water; the reaction of water with the resulting mixed halo(tert-butoxy)silanes leads to the formation of crosslinked siloxane products which even further reduce the efficiency of the alcoholysis to form trialkoxysilanes.

The prior art contains a number of attempts to alleviate or circumvent the problems associated with hydrogen halide solubility in the reaction mixture. (C. Eaborn, Organosilicon Compounds, pp. 289–294, Butterworths, London, 1960). These attempts include the use of hydrogen halide acceptors, e.g., amines, the use of solvents to reduce hydrogen halide solubility in the reaction medium, as well as the use of low pressure to pump off the hydrogen halide, as it is formed. (W. Gerard and K. Kilburn, J. Chem. Soc. (1956), p. 1536). None of these methods, however, has been very successful.

In current manufacturing practice, hydrogen halides evolved during the alcoholysis of halosilanes are treated as a waste product. Typically these hydrogen halides are scrubbed with water and the acidic solution is neutralized with base prior to final discharge. The recovery and reuse of chemically pure hydrogen halides, e.g., HCl, from the gaseous discharge of the halosilane alcoholysis for their use in the direct synthesis of trihalosilanes, e.g., trichlorosilane, is difficult and uneconomic because of the need to remove contaminants such as alcohols, solvents and other organic compounds down to insignificant levels.

In order to overcome the problems associated with the formation and removal of hydrogen halide from the conventional liquid phase alcoholysis reaction product, U.S. Pat. No. 4,395,564 to Kanner et al. discloses a new liquid phase process for the synthesis of trialkoxysilanes based on the alcoholysis of tris(dialkylamino)silanes, e.g., $HSi[N(CH_3)_2]_3$, in the presence of $CO_2$, dimethylammonium dimethylcarbamate (DI-CARB), protic acids or Lewis acids as catalyst.

This reaction is shown below in the following schematic reaction:

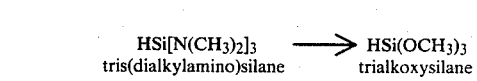

$$\underset{\text{tris(dialkylamino)silane}}{HSi[N(CH_3)_2]_3} \longrightarrow \underset{\text{trialkoxysilane}}{HSi(OCH_3)_3}$$

While the Kanner et al. patent avoids the problems of the prior art and helps to increase the efficiency of production of trialkoxysilanes such as $HSi(OCH_3)_3$, the reaction conditions taught by that patent, e.g., temperature and molar ratio, still result in a number of inefficiencies in this liquid-phase process.

For example, production of tetraalkoxysilane by-product seems to be more in the order of 10 to 30 weight percent than the 3 to 7 weight percent initially predicted in the patent. It appears that the dialkylamine, which is released during the reaction of tris(dialkylamino)silane, is retained in the reaction mixture as a by-product thus enhancing the loss of the Si—H bond on trialkoxysilane and aiding the formation of Si(OCH$_3$)$_4$. In addition, the Kanner patent also results in a significant amount, i.e., up to 11 percent, of by-products such as hydrido(dialkylamino) alkoxysilanes, e.g., $HSi[N(CH_3)_2]_x(OCH_3)_{3-x}$ where x equals 1 or 2 and dialkylamino-alkoxysilanes, e.g., $(CH_3O)_x Si[N(CH_3)_2]_{4-x}$ where x equals 1 to 3 which by-products persist in the reaction mixture even following the complete addition of 3 moles of alcohol to the DI-CARB plus tris(dialkylamino)silane mixture taught in the patent. If the crude reaction mixture is left in contact with dialkylamine by-product for at least a day, the concentration of these by-products rises even further, while conversely the concentration of trialkoxysilane decreases.

Thus there is no teaching in the art which recognizes that the retention of dialkylamine in the product mixture can cause an increase in the formation of tetraalkoxysilane or which recognizes the problem of redistribution of alkoxy and dialkylamino moieties on silicon leading to the persistence of dialkylaminoalkoxysilanes in the reaction product. Thus, there is a need in the art for a vapor-phase reaction of alcohol with various aminosilanes and carbamatosilanes to more efficiently produce alkoxysilanes, more particularly trialkoxysilanes, and reduce the level of undesirable by-products.

OBJECTIVES

It is thus an objective of this invention to provide a vapor-phase process between various silanes and alcohols for more efficiently producing alkoxysilanes, more particularly trialkoxysilanes.

It is a further object of this invention to provide such a process which simultaneously eliminates the concentration of undesirable by-products.

It is an even further object of this invention to provide a continuous or batch process in which by-products are recovered and subsequently reused.

Other objects and advantages of the invention will become apparent as the description thereof proceeds.

BRIEF SUMMARY OF THE INVENTION

In satisfaction of the foregoing objectives, this invention provides a novel vapor-phase reaction of aminosilanes, alkoxyaminosilanes, aminocarbamatosilanes, alkoxycarbamatosilanes and alkoxyaminocarbamatosilanes with alcohols for the synthesis of alkoxysilanes. More particularly, this invention is a catalytic vapor-phase reaction in which less than the stoichiometric amount of alcohol to silane is generally employed.

According to the invention, there is provided a full conversion of alcohol and partial conversion of the silane, e.g., aminosilane, per pass through the reactor and a recycling of the unreacted and partially reacted silane.

The instant invention provides a vapor phase alcoholysis process for reacting silanes of general formula:

$$HSi(NRR')_x(R'')_{3-x} \quad (II)$$

wherein R, R' and R'' may be aliphatic or aromatic, saturated or unsaturated hydrocarbon radicals having one to eight carbon atoms, inclusive, and R and R' may also be hydrogen, and R'' may also be alkoxy or carbamato, and x ranges from one to three, with alcohols of the general formula III:

$$R'''OH \quad (III)$$

wherein R''' is an aliphatic or aromatic, saturated or unsaturated, substituted or unsubstituted hydrocarbon radical having from one to twenty carbon atoms, inclusive, in which both the silane and the alcohol are present in the vapor-phase in a stoichiometric ratio of generally less than one mole of alcohol per mole of silicon-nitrogen functionality. The process affords unexpectedly high yields of hydridoalkoxysilanes and insignificant conversion of the SiH linkage on hydridoalkoxysilane to SiOR''' compared to the results obtained in liquid phase catalytic processes. As noted, the instant invention is also characterized by the recovery and reuse of the by-products of the vapor-phase alcoholysis reaction.

By using a vapor-phase reaction versus a liquid phase reaction and by recycling the unreacted or partially reacted silane, unexpectedly high yields of alkoxysilane, i.e., trialkoxysilane, are provided.

DETAILED DESCRIPTION OF THE INVENTION

The present invention provides a catalytic vapor-phase alcoholysis process for the synthesis of an alkoxysilane from an aminosilane and an alcohol, and/or from a carbamatosilane and an alcohol. The process comprises introducing a gaseous alcohol stream, a gaseous aminosilane stream, which may or may not be mixed beforehand with the gaseous carbamatosilane stream, into a heated reaction zone. A gaseous catalyst stream which may be separate from the other gaseous streams or admixed with either or all of them, is also introduced into the heated reaction zone. The alcohol, aminosilane, carbamatosilane, catalyst and reaction products are all maintained in the gaseous or vapor state for a period of time sufficient to effect complete or essentially complete conversion of the alcohol to an alkoxysilane. The mixture of vapors is thereafter cooled to temperatures whereby the desired alkoxysilane products are condensed and recovered and the reaction by-products and unreacted starting materials are recovered for subsequent reuse.

Reactants

The silanes useful in the process of the present invention are represented by the general formula:

$$HSi(NRR')_x(R'')_{3-x} \quad (II)$$

wherein R, R' and R'' are individually hydrogen, an aryl group or an alkyl group optionally containing unsaturation each having from one to eight carbon atoms inclusive, and where R'' may also be alkoxy or carbamato and where x has a value from one to three. Preferably, R, R' and R'' are independently an alkyl group having one to six carbon atoms, inclusive and x is two or three. Most preferably, the R and R' are each a methyl group and x is three.

Suitable silanes of Formula II which may be employed in the process include, but are not limited to, dimethylaminomethylethylsilane, diethylaminomethylpropylsilane, methylaminomethylethylsilane, ethylaminomethylethylsilane, phenylaminomethylethylsilane, benzylaminomethylphenylsilane, diphenylaminomethylphenylsilane, dibenzylaminomethylphenylsilane, dimethylaminodimethylsilane, diethylaminodimethylsilane, methylaminodimethylsilane, ethylaminodimethylsilane, diphenylaminodimethylsilane, dibenzylaminodimethylsilane, phenylaminodimethylsilane, benzylaminodimethylsilane, bis-dimethylaminomethylsilane, bis-diethylaminomethylsilane, bis-methylaminoethylsilane, bis-ethylaminoethylsilane, bis-diphenylaminoethylsilane, bis-benzylaminoethylsilane, bis-phenylaminomethylsilane, bis-benzylaminomethylsilane, bis-dimethylaminophenylsilane, bis-diethylaminophenylsilane, bis-ethylaminophenylsilane, bis-ethylaminopropylsilane, bis-diphenylaminopropylsilane, bis-dibenzylaminopropylsilane, tris-dimethylaminosilane, tris-diethylaminosilane, tris-methylaminosilane, tris-ethylaminosilane, tris-diphenylaminosilane, tris-dibenzylaminosilane, tris-phenylaminosilane, tris-benzylaminosilane, dicyclopentylaminomethylethylsilane, cyclopentylaminodimethylsilane, dicyclohexylaminodimethylsilane, cyclohexylaminodimethylsilane, bis-dicyclopentylaminomethylsilane, bis-cyclopentylaminomethylsilane, dicyclopentylaminodiphenylsilane, bis-dicyclopentylaminophenylsilane, tris-dicyclopentylaminosilane, cyclohexylaminodiphenylsilane, bis-cyclohexylaminomethylsilane, tris-cyclohexylaminosilane, tris(piperidino)silane and the like. Preferably the silane is tris(dimethylamino)silane.

The silane may be used alone or in mixtures with the products of its partial alcoholysis. For instance, when x equals 3 in Formula II, examples of the by-products of partial alcoholysis are compounds of the general formulae: $HSi(NRR')_y(OR''')_{3-y}$, $HSi(OOCNRR')_y(OR''')_{3-y}$, $HSi(OOCNRR')_y(NRR')_{3-y}$, y being 1 or 2, and $HSi(OOCNRR')(NRR')(OR''')$. The carbamato linkage (OOCNRR') results when carbon dioxide and its amine complexes are used as catalysts. Where the catalyst is carbon disulfide ($CS_2$) or carbonyl sulfide (COS) and their amine complexes, the corresponding dithiocarbamato and monothiocarbamato compounds are formed, for example, $HSi(SSCNRR')_y(OR''')_{3-y}$, $HSi(OSCNRR')_y(OR''')_{3-y}$ and so forth. When the preferred silane, tris(dimethylamino)silane, is used in a vapor-phase methanolysis and the catalyst is carbon dioxide, the following partial methanolysis products are produced and may be admixed with the desired trimethoxysilane: $HSi[OOCN(CH_3)_2]_y(OCH_3)_{3-y}$, $HSi[N(CH_3)_2]_y(OCH_3)_{3-y}$ and $HSi[OOCN(CH_3)_2]_y[N(CH_3)_2]_{3-y}$, y being 1 or 2. Other catalysts are discussed more generally below.

The preferred tris(dimethylamino)silane used in the instant process is conveniently synthesized by the direct process of reacting copper activated silicon with dimethylamine as disclosed in U.S. Pat. No. 4,255,348. However, it should be noted, this direct process produces a mixture of compounds along with the desired tris(dimethylamino)silane. It is preferable therefore, but not necessary, that the tris(dimethylamino)silane formed in that process be purified, e.g., by distillation, prior to use in the vapor-phase alcoholysis of the instant invention.

Alcohols

The alcohols useful in the process of the present invention are represented by the general formula:

R'''OH   (III)

wherein R''' is an aryl group or an alkyl group optionally containing unsaturation, having from one to twenty carbons, inclusive. Preferably, R''' is an alkyl group of from one to six carbon atoms, inclusive and most preferably the alcohol is either methanol or ethanol. The process of the present invention should be understood to be capable of employing the alcohol in a pure state or in admixture with other alcohols. However the alcohol must be essentially free of water, aldehydes and other impurities which can cause undesirable side reactions leading to solid formation and the loss of SiH functionality.

It should be noted that more sterically demanding alcohols undergo reaction less readily and in some instances do not react in the absence of the catalyst. Examples of the alcohols which may be used in the above process include, but are not limited to, methanol, ethanol, n-propanol, i-propanol, n-butanol, i-butanol, t-butanol, cyclohexanol, phenol, benzyl alcohol, n-apthanol, 3-ethylhexan 1-ol, 3-ethylhexan 2-ol, menthol, cholesterol, 4-methylbenzyl alcohol, m-chlorophenol, isoamylalcohol, neopentylalcohol, 2-methylaminoethanol, 2-dimethylaminopropan 1-ol, nonanol, 2-methoxyethanol, 2-ethoxyethanol, 2-methyl 3-butyne 2-ol, 3-methyl 1-pentyne 3-ol, thioethanol and the like.

Catalysts

The vapor-phase process is a catalyzed one and the catalyst may be carbon dioxide, carbonoxy sulfide, carbon disulfide or amine complexes thereof. Some examples of amine complexes which are effective in the above process include, but are not limited to, dimethylammonium dimethylcarbamate, diethylammonium diethylcarbamate, dipropylammonium dipropylcarbamate, dibutylammonium dibutylcarbamate, ammonium carbamate, methylammonium methylcarbamate, diphenylammonium diphenylcarbamate, phenylammonium phenylcarbamate, benzylammonium benzylcarbamate, dibenzylammonium dibenzylcarbamate, dimethylammonium dimethylcarbamate, methylammonium ethylcarbamate, diphenylammonium dimethylcarbamate, dimethylammonium diphenylcarbamate, diethylammonium dibenzylcarbamate, dibenzylammonium diethylcarbamate, phenylammonium dimethylcarbamate, methylammonium diphenylcarbamate and the like.

Whereas U.S. Pat. No. 4,395,564 to Kanner et al. (column 4, lines 14–26) teaches that protic acids, such as HCl, and Lewis acids, such as $AlCl_3$ and $FeCl_3$, are also catalysts for the liquid phase alcoholysis process, it has been found that the use of these halide-containing catalysts in the vapor phase process results in a drastic loss of the SiH functionality. The SiH bond is cleaved to give SiCl, for example, and eventually a tetraalkoxysilane is formed. Accordingly, metal halides and hydrohalic acids are not useful as catalysts for the instant vapor-phase alcoholysis process. In a preferred embodiment of the invention, the catalyst used is carbon dioxide provided as a gas or in the form of a carbamate.

It has been found that for the vapor-phase process, wherein a principal objective is to minimize or avoid conversion of the hydrosilane linkage of the trialkoxy compound to the alkoxysilane linkage, the optimum catalyst loading and the optimum alcohol to aminosilane stoichiometry are dependent on the particular alcohol being used. The broad range of catalyst concentrations is from 0.01 to 10 mole percent based on the amount of silicon-nitrogen bonds. For vapor-phase methanolysis the optimum catalyst level is 2.0 to 6.0 mole percent based on the molar content of silicon-nitrogen bonds being reacted and more preferably 3.5 to 5.0 mole percent. The optimum molar ratio of methanol to silicon-nitrogen bonds is 0.45 to 0.95 and more preferably 0.55 to 0.85. On the other hand, vapor-phase ethanolysis of the aminosilane is most advantageously conducted at a catalyst loading of 0.25 to 2.0 mole percent of the silicon-nitrogen bonds being reacted and a molar ratio of ethanol to silicon-nitrogen bonds of 0.65 to 0.95, more preferably, 0.75 to 0.95. With sterically hindered alcohols such as t-butanol, a catalyst concentration of 0.75 to 1.25 mole percent is also preferred, but the alcohol to aminosilane stoichiometry could be 1.0 and even as much as 1.05. There are particular advantages in the use of a preferred range for vapor-phase methanolysis that is discouraged as costlier and unbeneficial by the batchwise liquid phase process. As noted, the preferred range of molar ratios of alcohol to silicon-nitrogen bonds for vapor-phase methanolysis is defined as 0.55 to 0.85; for vapor-phase ethanolysis, n-propanolysis and isopropanolysis as 0.75 to 0.95; and for t-butanolysis as 0.80 to 1.05.

The reaction conditions are such that the catalyzed reaction may be carried out with or without solvent. In most cases there is no particular advantage to using a solvent. However, a solvent may be in some cases desirable, such as to improve solubility or temperature control. If a solvent is used, it should not contain an active hydrogen such as those found in alcohols or amines. Examples of suitable solvents are hydrocarbons such as hexane, and toluene or the like.

The temperature of the catalytic vapor phase alcoholysis process must exceed the boiling points of the reactants, catalyst and products. The boiling point referred to is not necessarily the normal boiling point (that is, the boiling point at 1 atmosphere absolute pressure) but that which is appropriate to the pressure conditions of the reactor. Thus the temperature of the reaction zone should be at least as high as the boiling point of the highest boiling component determined under the reaction zone conditions, preferably at least 5° C. greater than the boiling point of the highest boiling component of the reaction mixture as determined under the reaction zone conditions.

The maximum temperature for the reaction zone is not narrowly critical. It should not be so high as to cause the reactants, catalyst and products to undergo thermal decomposition and/or to engage in reactions other than the desired alcoholysis. Thus, the maximum temperature for the vapor-phase alcoholysis should be below the thermal decomposition temperatures of the reactants and products and should also be less than the temperature at which the materials of construction of the reactor are attacked by the reactants, catalyst and products of the vapor-phase alcoholysis. This latter consideration is one of engineering design and is within the skill of the chemist or engineer. In general, the temperature of the reaction zone should not exceed the boiling point of the highest boiling component in the reactants and products by more than 150° C. Consequently, the selection of the most desirable temperature range employable in the practice of this invention is dependent upon the specific aminosilane and alcohol selected. The optimum temperature range for the carbon dioxide catalyzed vapor-phase alcoholysis of tris(-dimethylamino)silane with alcohols having 1 to 4 carbons at 1 atmosphere absolute is about 200°–250° C. The optimum ranges for additional vapor-phase alcoholysis reactions are readily determined by those skilled in the art of vapor-phase reactions.

The vapor-phase alcoholysis may be conducted at a variety of pressures. Pressures ranging from sub-atmospheric to atmospheric to super-atmospheric may be employed. The exact pressure conditions will be dependent upon the boiling point of the reactants and products, the susceptibility of the reactants and products to decomposition at certain temperatures and pressures and the like considerations. For example, if the boiling point of the alkoxysilane products is inordinately high and its stability to decomposition is adversely affected when operating at atmospheric pressure, then it will be desirable in such cases to operate the vapor-phase alcoholysis process at lower than atmospheric pressure. Pressures as low as 1 millimeter of mercury and lower may be employed. Conversely, with reactants or products which are extremely volatile at atmospheric pressure, the process may be run under super-atmospheric pressure to ensure safe and economic operation. In most cases, atmospheric pressure will be found to be the most desirable and economical to employ.

Residence or contact time of the reactants in the reaction zone is calculated by dividing the volume of the reaction zone by the volumetric flow rate of the reactants. Thus if the reactor volume is 100 milliliters and the total flow (determined at the reactor temperature) of reactants into the reactor is 65 milliliters per second, then the residence time of the reactants in the reaction zone is 1.54 seconds The residence time employed is dependent upon the reactivity of the aminosilane and alcohol. Its value is also determined by the temperature of the vapor-phase alcoholysis. Higher temperatures lead to higher volumetric flow rates and hence to shorter residence times. Typically, the contact time will not exceed 60 seconds. Values of 1 to about 20 seconds have been generally employed for the instant invention and values in the range, 1.5 to 5.0 seconds are preferred.

The process of the instant invention can be operated in a continuous or batch mode. The mode of operation selected is dependent upon factors such as the scale of the alkoxysilane synthesis and the cost and availability of suitable equipment. The principal difference between these two modes of operation is that, in the continuous process, distillation and recovery of the desired alkoxysilane and the reaction by-products occur, without interruption, immediately following the vapor-phase alcoholysis. In the batch mode the vapor-phase alcoholysis product is collected and distillation is performed later in equipment not directly joined to the vapor-phase reactor.

In a preferred embodiment, the present invention is a process for the catalytic vapor-phase synthesis of trialkoxysilanes, i.e., compounds of general formula, $HSi(OR''')_3$ which process comprises introduction of a gaseous alcohol stream, a gaseous tris(dialkylamino)silane stream, which may or may not be mixed beforehand with a gaseous stream of carbamatosilanes of general formulae $HSi(OCONRR')_x(OR''')_{3-x}$ or $HSi(NRR')_x(OCONRR')_{3-x}$ wherein R, R' and R''' have the meaning defined above and x may be 0, 1 or 2, each separately into a heated reaction zone and a gaseous catalyst stream, which may be separate from the other gaseous streams or admixed with either or all of them, also into the heated reaction zone and maintaining the alcohol, tris(dialkylamino)silane, carbamatosilane, catalyst and reaction products all in the gaseous or vapor state for a period of time sufficient to effect complete or essentially complete conversion of the alcohol to an alkoxysilane. The mixture of vapors is thereafter cooled to temperatures whereby the desired alkoxysilane products are condensed and recovered and the reaction by-products and unreacted tris(dialkylamino)silane are recovered for subsequent reuse.

A specially preferred embodiment of the present invention is the catalytic vapo phase alcoholysis process wherein the alcohol is methanol, the aminosilane is tris(dimethylamino)silane, the catalyst is carbon dioxide provided as a gas or in the form of a carbamate (i.e., DI-CARB). The desired alkoxysilane product is trimethoxysilane and the liquid mixture of by-products containing unreacted tris(dimethylamino)silane, methoxyaminosilanes of general formula $HSi(OCH_3)_x[N(CH_3)_2]_{3-x}$, aminocarbamatosilanes of general formula $HSi[N(CH_3)_2]_x[OCON(CH_3)_2]_{3-x}$, and methoxycarbamatosilanes of general formula $HSi(OCH_3)_x[OCON(CH_3)_2]_{3-x}$, x being 1 or 2, is mixed with additional tris(dimethylamino)silane and recycled to the catalytic vapor-phase process.

Whereas the exact scope of this instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLES

The apparatus consists of the following distinct units: The tris(dimethylamino)silane feed system, which is made up of a tris(dimethylamino) silane reservoir, a pump, a bursting disc and a pressure gauge; alcohol feed system, which contains an alcohol reservoir and alcohol pump; a vapor phase reactor; a condenser assembly, and crude product storage.

The tris(dimethylamino)silane reservoir is a glass or stainless steel container, about 1 liter in volume. The stainless steel (⅛ inch o.d.) transport line from the reservoir to the pump is attached to the reservoir with gas-tight fittings. A nitrogen-flushed vent-line is also similarly connected to the reservoir. The reservoir is attached to a gravimetric measuring device such as a load-cell or balance. The transport line between the reservoir and pump is bent to allow for a syphoning action and the absence of vapor locks.

The pump should be corrosion resistant, preferably with a ceramic cylinder and piston. The pump is used to deliver the tris(dimethylamino)silane to the vaporizer. Stainless steel tubing (⅛ inch) connects the pump and vaporizer. The pump is provided with a micrometer flow controller which permits calibration. A suitable pump is the RP-SY pump manufactured by Fluid Metering Inc. (FMI ®). The pump and reservoir are housed in an enclosure which is kept flushed with dry nitrogen in order to prevent reaction of the aminosilane with atmospheric moisture. If the pump head is not so protected it may seize and break.

The pressure gauge registers the tris(dimethylamino)silane fluid pressure in the line between the pump and vaporizer. The gauge may have any readable full scale setting greater than 15 psig. In laboratory practice, line pressure is maintained at <15 psig to prevent breakage of glass components. A 15 psig bursting disc, in a tee just downstream of the gauge, provides the assurance against such breakage.

A 100 cm$^3$ stainless steel cylinder with ¼ inch opening at each end serves as the aminosilane vaporizer. The cylinder is packed with ⅛ inch by 3/16 inch perforated stainless steel saddles (PROPAK ® from Chem-Pro, Inc.). Thermocouples are provided at the vaporizer outlet and between the vaporizer wall and its heating jacket to monitor and control the temperature of the vaporizer. The heating jacket is wound heating tape or heating wire or a heating mantle which is safely electrically insulated from the stainless steel cylinder. Thermal insulation, e.g., fiberglass, is used to wrap the vaporizer and its heater and the transport line between the vaporizer and the reactor.

A catalyst delivery system is used for gaseous catalysts such as carbon dioxide. The system begins distally with a carbon dioxide cylinder with the appropriate regulator connected to a drying tube packed with DRIERITE ® and/or LINDE 4A molecular sieve with ¼ inch stainless steel tubing. A calibrated flowmeter follows. The line between the dryer and the flowmeter contains a valved tee for the introduction of dry nitrogen when the apparatus is being purged. A valved tee also connects the stainless steel tubing from the outlet of the flowmeter to the thermally insulated line between the vaporizer and the reactor. When liquid or solid catalysts are employed they may be dissolved in the alcohol and added along with it to the reactor.

The alcohol reservoir is a glass or stainless steel container about 0.5-1.0 liter in volume. It is attached to a calibrated RP-SY FMI pump via ⅛ inch stainless steel tubing. The alcohol reservoir may be graduated volumetrically and/or optionally interfaced with a load cell or balance for gravimetric recording of the alcohol delivered to the reactor. The alcohol reservoir and pump are fully surrounded by an enclosure flushed with dry nitrogen. The alcohol transport line from the pump to the vapor phase reactor is coiled along the outside of the reactor and actually functions as the alcohol vaporizer.

The vapor phase reactor is a 30 inch long, ½ inch diameter stainless steel tube fitted with a half-inch cross at its inlet. One port of the cross accepts the vaporized aminosilane and carbon dioxide feed, another accepts the vaporized alcohol, which may also contain catalyst, and the third accepts a multi-point thermocouple for measurement of temperature at selected points along the length of the reactor. Three additional thermocouples are located along the external surface of the vapor phase reactor. They are wired to the heater controller and are used to control the temperature of the reactor. The heater and reactor are wrapped in a thick layer of thermal insulation (e.g., glass wool or fiberglass). At its outlet the vapor phase reactor has a screen, held in place by a half-inch tubing fitting for the retention of packing material. The reactor is optionally packed with 3/16 by ⅛ inch stainless steel or ceramic saddles. The attachment of the vapor phase reactor to the condensing unit is made with a Y tube having a metal to glass joint.

The condenser assembly is a combination of water-cooled condensers and distillation columns in series to permit separation of the gaseous dimethylamine from the higher boiling alkoxysilanes, aminosilanes and alcoholysis by-products. A double surface condenser is attached to the upper end of the Y tube and a Friedrich condenser to the top of the double surface condenser. Copper tubing is optionally coiled around both condensers for the circulation of cold water or a refrigerant. At the outlet of the Friedrich condenser is a tee with attachments for a nitrogen vent flow. A gas cylinder cooled in liquid nitrogen or dry-ice/isopropanol is attached directly to the outlet of the Friedrich condenser. The lower end of the Y tube connects the distillation column (e.g., 5 plate Oldershaw column) to the double surface condenser. Liquid which is condensed on the cooled surfaces of the condensers is stripped of dimethylamine during passage down the Oldershaw column and it eventually enters the storage/sampling flask attached to the lower end of the Oldershaw column.

The storage/sampling flask is a 500 ml or 1000 ml 4-neck round bottom flask. The distillation column is affixed in one neck, a thermocouple in another, a nitrogen sparge in the third and a siphon device for sampling in the fourth.

Materials:

The alcohols used in the following examples were commercially available, reagent grade compounds.

Tris(dimethylamino)silane was synthesized by the method of U.S. Pat. No. 4,255,348 and was distilled (bpt 142°) prior to use. Dimethylammonium dimethylcarbamate (DICARB) was synthesized by the co-reaction of $CO_2$ and $(CH_3)_2NH$ as described in U.S. Pat. No. 2,927,129. The carbon dioxide used was commercially available anhydrous gas packaged in standard steel cylinders.

General Procedure

Samples of the vapor phase reaction products were analyzed by gas chromatography.

The catalyst (DICARB) and $CO_2$ levels in the reaction product were monitored by gas chromatographic analysis. It was determined experimentally that DICARB decomposes smoothly during analysis (column temperature, 90° C.) to 32.9±1.33 wt. % $CO_2$ and 66.7±1.30 wt % $(CH_3)_2NH$. The theoretical values are 32.8 wt. % $CO_2$ and 67.2 wt. % $(CH_3)_2NH$. Accordingly, the level of $CO_2$ present in a sample is indicative of the DICARB catalyst concentration. Carbon dioxide concentrations were also analyzed in standard samples prepared from $[(CH_3)_2N]_3SiH$ and DICARB. DICARB was present in the range 1.25–10 mole %. A DICARB level of 5 mole % was equivalent to a $CO_2$ value of 1.5–1.6 wt. % by gas chromatography.

Defininitions

TRIM = $HSi(OCH_3)_3$
DMAS = $HSi(OCH_3)_2[N(CH_3)_2]$
DAMS = $HSi[N(CH_3)_2]_2(OCH_3)$
TRIS = $HSi[N(CH_3)_2]_3$
TETM = $Si(OCH_3)_4$
DEAS = $HSi(OC_2H_5)_2[N(CH_3)_2]$
DAES = $HSi[N(CH_3)_2](OCH_2H_5)$
TRIE = $HSi(OC_2H_5)_3$
TETE = $Si(OC_2H_5)_4$
TRIP = $HSi[OCH(CH_3)_2]_3$
DMA = $HN(CH_3)_2$
DIES = $H_2Si(OC_2H_5)_2$
MMA = $H_2NCH_3$
TMA = $N(CH_3)_3$
TEAS = $[(CH_3)_2N]Si(OC_2H_5)_3$
DICARB = $[(CH_3)_2NH_2]^+[OOCN(CH_3)_2]^-$
DBAS = $HSi[OC_4H_9\text{-tert}]_2[N(CH_3)_2]$
TTBS = $HSi[OC_4H_9\text{-tert}]_3$
LIGHTS = Low boiling fraction from reaction or distillation. See tables for specific composition.
HVS = Higher boiling fraction from a reaction or distillation. See tables for specific composition.
tr = trace levels
°C. = degree Celsius
min = minute
hr = hour
sec = second
ml = milliliter
lit = liter
gm = gram
gc = gas chromatography
gc/ms = gas chromatography/mass spectrometry
i.d. = internal diameter
o.d. = outer diameter
N.D. = not detected
N.A. = not analyzed
TCD = Thermal Conductivity Detector

EXAMPLE 1—EFFECT OF CATALYST CONCENTRATION ON VAPOR PHASE METHANOLYSIS

This example illustrates that the catalyst level (expressed as a molar percentage of the SiN bonds) affects the retention of SiH bonds and minimization of the formation of tetraalkoxysilane.

The vapor phase reactor was heated to 200° C. and the $HSi[N(CH_3)_2]_3$ vaporizer to 220° C. $CH_3OH$ flow rate of 2.69 gm/min and $HSi[N(CH_3)_2]_3$ flow rate of 6.35 gm/min were held constant for the duration of the experiment, 425 minutes. The molar ratio of methanol to SiN bonds was 0.71. Carbon dioxide flow rates were chosen as shown in Table 1 in order to obtain catalyst levels between 1 and 10 mole % based on the SiN bonds. Samples for gas chromatographic analysis were taken at the times shown. Note that the reaction was allowed to stabilize following a catalyst concentration change before an analytical sample was withdrawn.

The data of Table 1 show that the tetramethoxysilane content of the vapor phase alcoholysis product was less than 1 percent for catalyst ($CO_2$) concentrations greater than or equal to 2 mole % of the SiN bonds and was typically less than or equal to 0.6 percent at catalyst concentrations of about 2 mole percent.

TABLE 1

EFFECT OF CATALYST (CARBON DIOXIDE) CONCENTRATION ON THE FORMATION OF TETRAMETHOXYSILANE AND THE CONVERSION OF TRIS(DIMETHYLAMINO)SILANE

| Time (min) | $CO_2$ cm³/min | Mole % Catalyst | $CO_2$ Area % | LIGHTS Area % | TRIM Area % | DMAS Area % | TETM Area % | DAMS Area % | TRIS Area % | HVS Area % |
|---|---|---|---|---|---|---|---|---|---|---|
| 0 | 246 | 8.63 | | | | | | | | |
| 62 | 246 | 8.63 | 9.7 | 2.6 | 30.4 | 33.2 | 0.1 | 19.2 | 4.2 | 0.5 |
| 67 | 113 | 3.96 | | | | | | | | |
| 105 | 113 | 3.96 | 2.2 | 3.4 | 35.8 | 37.1 | 0.1 | 15.3 | 5.0 | 1.1 |
| 128 | 113 | 3.96 | 2.8 | 2.2 | 35.8 | 37.6 | 0.3 | 15.8 | 4.4 | 1.0 |
| 130 | 28 | 0.98 | | | | | | | | |
| 204 | 28 | 0.98 | 0.8 | 1.7 | 48.7 | 15.1 | 3.2 | 2.7 | 27.1 | 0.6 |
| 237 | 28 | 0.98 | 0.9 | 1.8 | 49.3 | 15.0 | 3.4 | 2.7 | 26.4 | 0.5 |
| 240 | 57 | 2.00 | | | | | | | | |
| 297 | 57 | 2.00 | 1.5 | 1.8 | 45.4 | 26.7 | 0.6 | 6.6 | 16.2 | 1.1 |
| 318 | 57 | 2.00 | 1.6 | 2.0 | 45.8 | 27.9 | 0.4 | 6.9 | 14.2 | 1.2 |
| 328 | 28 | 0.98 | | | | | | | | |
| 368 | 28 | 0.98 | 0.4 | 2.1 | 50.7 | 15.0 | 2.8 | 2.6 | 25.2 | 1.2 |
| 388 | 28 | 0.98 | 0.5 | 2.2 | 50.2 | 13.8 | 3.5 | 2.4 | 26.5 | 0.9 |
| 391 | 113 | 3.96 | | | | | | | | |

TABLE 1-continued

EFFECT OF CATALYST (CARBON DIOXIDE) CONCENTRATION ON THE FORMATION OF
TETRAMETHOXYSILANE AND THE CONVERSION OF TRIS(DIMETHYLAMINO)SILANE

| Time (min) | $CO_2$ cm³/min | Mole % Catalyst | $CO_2$ Area % | LIGHTS Area % | TRIM Area % | DMAS Area % | TETM Area % | DAMS Area % | TRIS Area % | HVS Area % |
|---|---|---|---|---|---|---|---|---|---|---|
| 425 | 113 | 3.96 | 4.4 | 2.2 | 36.1 | 36.0 | 0.6 | 15.4 | 4.5 | 0.8 |

Note:
LIGHTS = Mostly $HN(CH_3)_2$ plus $H_2NDH_3$ and traces of methanol.
HVS = $H(CH_3O)_2SiOSi(OCH_3)_2H$, $H(CH_3O)_2SiOSi(OCH_3)_3$, $(CH_3O)_3SiOSi(OCH_3)_3$, $HSi[OOCN(CH_3)_2]_x[N(CH_3)_2]_{3-x}$ (x = 1,2,3), $HSi[OOCN(CH_3)_2]_x(OCH_3)_{3-x}$ (x = 1,2,3), $CH_3OSi[OOCN(CH_3)_2]_x(OCH_3)_{3-x}$ (x = 1,2,3), $CH_3OSi[N(CH_3)_2]_x(OCH_3)_{3-x}$ (x = 1,2,3) and $CH_3OSi[OOCN(CH_3)_2]_x[N(CH_3)_2]_{3-x}$ (x = 1,2,3).

EXAMPLE 2—EFFECT OF REACTOR TEMPERATURE

This example illustrates that temperatures in the range 150°–300° C. and superficial contact times of about 1–1.4 sec are suitable for carrying out the vapor phase methanolysis of tris(dimethylamino)silane. The procedure of Example 1 was followed except as noted hereinbelow. The $CO_2$ flow rate was set at 113 cm³/min and corresponded to a catalyst level of 4.09 mole % based on the SiN bonds. The liquid flow rates of $CH_3OH$ and $HSi[N(CH_3)_2]_3$ were 2.50 gm/min and 6.13 gm/min, respectively. The duration of the experiment was 352 minutes. Samples were withdrawn for gas chromatographic analysis after the vapor phase reaction had been allowed sufficient time to achieve steady-state at the new temperature. The data are set forth in Table 2.

It can be seen that the amount of unreacted tris(dimethylamino)silane was least at 300° C. and most at 150° C. Tetramethoxysilane was less than or equal to 0.4% throughout the entire temperature range studied. The data also show that satisfactory results were obtained at superficial contact times as short as 1.0–1.4 secs.

TABLE 2

THE EFFECT OF THE VAPOR PHASE REACTOR TEMPERATURE ON
THE METHANOLYSIS OF TRIS(DIMETHYLAMINO)SILANE

| Time (min) | Temp. °C. | Contact Time (sec) | $CO_2$ Area % | LIGHTS Area % | TRIM Area % | DMAS Area % | TETM Area % | DAMS Area % | TRIS Area % | HVS Area % |
|---|---|---|---|---|---|---|---|---|---|---|
| 0 | 150 | 1.38 | | | | | | | | |
| 53 | 150 | 1.38 | 1.3 | 3.3 | 41.0 | 26.0 | 0.3 | 8.4 | 18.4 | 1.3 |
| 74 | 150 | 1.38 | 1.7 | 2.8 | 40.9 | 27.4 | 0.2 | 7.8 | 18.1 | 1.1 |
| 95 | 150 | 1.38 | 1.7 | 2.4 | 40.8 | 29.2 | 0.2 | 8.4 | 15.8 | 1.5 |
| 97 | 200 | 1.23 | | | | | | | | |
| 155 | 200 | 1.23 | 1.9 | 2.3 | 43.8 | 28.9 | 0.2 | 7.8 | 13.6 | 1.5 |
| 177 | 200 | 1.23 | 2.3 | 2.4 | 41.5 | 31.0 | 0.2 | 9.3 | 12.2 | 1.1 |
| 180 | 250 | 1.12 | | | | | | | | |
| 237 | 250 | 1.12 | 2.4 | 1.3 | 44.8 | 30.7 | 0.2 | 8.5 | 10.4 | 1.5 |
| 262 | 250 | 1.12 | 2.7 | 1.7 | 42.1 | 31.4 | 0.2 | 9.3 | 11.2 | 1.4 |
| 286 | 250 | 1.12 | 2.2 | 2.1 | 42.0 | 32.2 | 0.1 | 9.9 | 9.8 | 1.7 |
| 297 | 300 | 1.02 | | | | | | | | |
| 352 | 300 | 1.02 | 2.8 | 1.5 | 42.5 | 34.0 | 0.4 | 11.2 | 6.0 | 1.5 |

Note:
LIGHTS = Mostly $HN(CH_3)_2$ plus $H_2NCH_3$ and traces of methanol.
HVS = $H(CH_3O)_2SiOSi(OCH_3)_2H$, $H(CH_3O)_2SiOSi(OCH_3)_3$, $(CH_3O)_3SiOSi(OCH_3)_3$, $HSi[OOCN(CH_3)_2]_x[N(CH_3)_2]_{3-x}$ (x = 1,2,3), $HSi[OOCN(CH_3)_2]_x(OCH_3)_{3-x}$ (x = 1,2,3), $CH_3OSi[OOCN(CH_3)_2]_x(OCH_3)_{3-x}$ (x = 1,2,3), $CH_3OSi[N(CH_3)_2]_x(OCH_3)_{3-x}$ (x = 1,2,3) and $CH_3OSi[OOCN(CH_3)_2]_x[N(CH_3)_2]_{3-x}$ (x = 1,2,3).

EXAMPLE 3

In this example the stoichiometry of alcohol to SiN bonds is varied in order to establish that range of stoichiometries yielding the minimum tetramethoxysilane formation. The reactor temperature was held constant at 200° C., and the flow rate of liquid tris(dimethylamino)silane was 6.35 gm/min. The catalyst used was DICARB at the concentration, 106.0 gm DICARB/500 gm methanol. The catalyst concentration was 5 mole % based on the SiN bonds.

Data for this example are set forth in Table 3. The table shows that for methanol:SiN molar ratios of 0.55–0.71, only trace levels (i.e., ≦0.05 wt. %) of tetramethoxysilane were formed during the vapor phase methanolysis of tris(dimethylamino)silane.

TABLE 3

EFFECT OF VARYING METHANOL TO SiN STOICHIOMETRY ON
TETRAMETHOXYSILANE FORMATION

| Time (min) | Methanol gm/min | RATIO $CH_3OH/$ SiN | LIGHTS Area % | TRIM Area % | DMAS Area % | TETM Area % | DAMS Area % | TRIS Area % | HVS Area % |
|---|---|---|---|---|---|---|---|---|---|
| 0 | 2.07 | 0.55 | | | | | | | |
| 53 | 2.07 | 0.55 | 2.5 | 32.0 | 26.7 | tr | 9.7 | 28.0 | 0.7 |
| 70 | 2.07 | 0.55 | 1.3 | 30.2 | 25.6 | tr | 8.9 | 32.9 | 0.9 |
| 72 | 2.19 | 0.58 | | | | | | | |
| 122 | 2.19 | 0.58 | 1.3 | 30.2 | 24.5 | tr | 8.4 | 24.8 | 0.5 |
| 133 | 2.19 | 0.58 | 1.2 | 29.4 | 25.1 | tr | 8.8 | 34.8 | 0.51 |
| 135 | 2.32 | 0.61 | | | | | | | |
| 173 | 2.32 | 0.61 | 1.4 | 31.5 | 25.9 | tr | 8.4 | 31.4 | 0.6 |
| 191 | 2.32 | 0.61 | 1.6 | 34.1 | 32.7 | tr | 11.8 | 19.2 | 0.5 |
| 194 | 2.44 | 0.65 | | | | | | | |
| 237 | 2.44 | 0.65 | 1.0 | 31.5 | 31.2 | tr | 12.3 | 23.3 | 0.5 |

TABLE 3-continued

EFFECT OF VARYING METHANOL TO SiN STOICHIOMETRY ON TETRAMETHOXYSILANE FORMATION

| Time (min) | Methanol gm/min | RATIO CH$_3$OH/ SiN | LIGHTS Area % | TRIM Area % | DMAS Area % | TETM Area % | DAMS Area % | TRIS Area % | HVS Area % |
|---|---|---|---|---|---|---|---|---|---|
| 267 | 2.44 | 0.65 | 1.0 | 31.4 | 32.5 | tr | 12.7 | 19.7 | 2.5 |
| 270 | 2.57 | 0.68 | | | | | | | |
| 321 | 2.57 | 0.68 | 1.0 | 33.0 | 30.0 | tr | 10.8 | 22.8 | 2.2 |
| 341 | 2.57 | 0.68 | 1.3 | 32.2 | 29.8 | tr | 10.6 | 25.9 | 0.9 |
| 343 | 2.69 | 0.71 | | | | | | | |
| 382 | 2.69 | 0.71 | 1.0 | 36.4 | 31.6 | tr | 11.2 | 16.6 | 3.0 |
| 397 | 2.69 | 0.71 | 1.2 | 35.5 | 31.7 | tr | 11.7 | 19.2 | 0.5 |

Note:
LIGHTS = Mostly HN(CH$_3$)$_2$ plus H$_2$NCH$_3$ and traces of methanol.
HVS = H(CH$_3$O)$_2$SiOSi(OCH$_3$)$_2$H, H(CH$_3$O)$_2$SiOSi(OCH$_3$)$_3$, (CH$_3$O)$_3$SiOSi(OCH$_3$)$_3$, HSi[OOCN(CH$_3$)$_2$]$_x$[N(CH$_3$)$_2$]$_{3-x}$ (x = 1,2,3), HSi[OOCN(CH$_3$)$_2$]$_x$(OCH$_3$)$_{3-x}$ (x = 1,2,3), CH$_3$OSi[OOCN(CH$_3$)$_2$]$_x$(OCH$_3$)$_{3-x}$ (x = 1,2,3), CH$_3$OSi[N(CH$_3$)$_2$]$_x$. (OCH$_3$)$_{3-x}$ (x = 1,2,3) and CH$_3$OSi[OOCN(CH$_3$)$_2$]$_x$[N(CH$_3$)$_2$]$_{3-x}$ (x = 1,2,3).

EXAMPLE 4

This example illustrates the recovery by distillation of trimethoxysilane from the crude vapor phase methanolysis reaction mixture.

The distillation apparatus consisted of a 3000 ml round bottom 3-neck flask attached to a 30-plate Oldershaw column. To the remaining two necks were attached a thermometer and a ground-glass stopper, respectively. The flask was heated with a heating mantle. A water-cooled condenser with magnetically controlled reflux system was affixed atop the Oldershaw column. The distillate from the condenser was collected in receiving flasks.

1642 gm of crude product prepared in Example 3 was added to the distilling flask and heated slowly. Distillation fractions were collected at the head temperatures shown in Table 4. From the composition of the fractions, the 1642 gm of crude product afforded 660 gm trimethoxysilane, which is more than that calculable from the composition of the starting material (first row of Table 4). The additional tri-methoxysilane was formed via the disproportionation of the mixed dimethylaminomethoxysilanes, e.g., HSi(OCH$_3$)$_2$[N(CH$_3$)$_2$]. The vapor phase methanolysis consumed 2521 gm tris(-dimethylamino)silane and 1005 gm methanol and produced a total of 1166 gm trimethoxysilane. The stoichiometric amount of trimethoxysilane obtainable from 1005 gm (31.4 moles) methanol is 1277 gm. So the yield of trimethoxysilane was 91.3 wt. % based on methanol converted. Note, however, that the methanol not converted to trimethoxysilane in this pass through the reactor was converted mainly to the mixed dimethylaminomethoxysilanes, e.g., HSi[N(CH$_3$)$_2$]$_2$(OCH$_3$), and mixed methoxydimethylcarbamatosilanes, e.g., HSi[OOCN(CH$_3$)$_2$]$_x$(OCH$_3$)$_{3-x}$ (x=1,2,3), which are recyclable. Only negligible quantities of Si(OCH$_3$)$_4$ were formed.

TABLE 4

| | RECOVERY OF TRIMETHOXYSILANE BY DISTILLATION (REFLUX RATIO 10:1) | | | | | | | | |
|---|---|---|---|---|---|---|---|---|---|
| Fraction Number | Pot Temp °C. | Head Temp °C. | Wt. gm | LIGHTS Area % | TRIM Area % | DMAS Area % | TETM Area % | DAMS Area % | TRIS Area % | HVS Area % |
| Starting Material | | | 1642 | 1.2 | 35.9 | 24.2 | 0.05 | 10.2 | 28.3 | 0.2 |
| 1 | 125 | 82–85 | 419 | 0.6 | 98.6 | tr | tr | — | — | |
| 2 | 135 | 85 | 162 | 0.4 | 96.4 | 2.9 | tr | tr | — | |
| 3 | 142 | 89 | 92 | 0.4 | 87.5 | 11.5 | tr | 0.4 | — | |
| Pot Residue* | | | 952 | 0.2 | 0.2 | 4.5 | 0.1 | 35.4 | 50.2 | 3.0 |

Notes:
*CO$_2$ peak amounted to 6.4 area %.
LIGHTS = DMA, H$_2$Si(OCH$_3$)$_2$, [(CH$_3$)$_2$N]$_2$CH$_2$.
HVS = (CH$_3$)$_2$NSi(OCH$_3$)$_3$, H(CH$_3$O)$_2$SiOSi(OCH$_3$)$_2$H and the methoxydimethylcarbamatosilanes described above.

EXAMPLE 5

This example illustrates that the pot residue from the distillation of Example 4 can be recycled to the vapor phase methanolysis reactor for the synthesis of additional trimethoxysilane. Each recycle experiment (5A, 5B, 5C) of this example consists of a vapor phase methanolysis followed by distillation of trimethoxysilane from the crude methanolysis product.

5A Vapor Phase Reaction

The pot residue (952 gm) from Example 4 was mixed with 1380 gm tris(dimethylamino)silane and reacted with methanol in the vapor phase reactor at 200° C. as described in Example 1. The aminosilane stream (i.e., TRIS plus pot residue), the composition of which is shown in Table 5, was fed to the reactor at 5.54–6.02 gm/min and the methanol stream at 1.57–2.19 gm/min. The pot residue contained an adequate amount of catalyst (CO$_2$ peak area=6.4% by gc) so no additional catalyst was added to the reactor or to the reagents. 748 gm methanol and 2166 gm of TRIS plus pot residue were consumed and the total weight of methanolysis product was 1718 gm. The composition of this product is also set forth in Table 5.

Distillation 1708 gm of the crude methanolysis product, having the composition shown in Table 5, was distilled as described in Example 4. Six fractions (See Table 6) containing a total of 870 gm trimethoxysilane were collected. The pot residue weighed 770 gm and showed 1.3 area % for CO$_2$ by gc.

5B Vapor Phase Reaction

Tris(dimethylamino)silane (1219 gm) was mixed with the pot residue (770 gm) from the distillation of Example 5A and reacted with methanol at 200° C. in the vapor phase reactor as described in Example 4. The methanol flow rate was varied between 1.95–2.19 gm/min and the aminosilane stream was maintained at 6.35 gm/min. No make up catalyst was added to the reagents or the reactor. The composition of the samples collected is set forth in Table 7. 745 gm methanol was consumed and 1516 gm crude product was collected.

Distillation 1506 gm of the vapor phase methanolysis product of Example 5B was distilled as described in Example 4. A total of 765 gm of trimethoxysilane was contained in the three fractions collected (see Table 8). The pot residue weighed 687 gm and showed a $CO_2$ peak area of 1.4% by gc.

5C Vapor Phase Reaction

The pot residue from the distillation of Example 5B was combined with 1318 gm tris(dimethylamino)silane and recycled to the vapor phase methanolysis at 200° C. The methanol flow rate was 1.95 gm/min; the aminosilane flow at 6.35 gm/min. 728 gm methanol was consumed and 1517 gm crude product was collected. Samples taken are described in Table 9.

Distillation 1507 gm of crude methanolysis product was distilled as described in Example 4. The three fractions taken contained 673 gm (see Table 10) trimethoxysilane altogether.

SUMMARY OF RECYCLE EXPERIMENTS

The results of Examples 3, 4 and 5 show that a single addition of DICARB catalyst was sufficient to convert 3,226 gm methanol and 6438 gm TRIS to 3,474 gm trimethoxysilane in four vapor phase reaction/distillation cycles. The content of tetramethoxysilane after four cycles was 1.1% (Table 10) or 0.18% per cycle. These examples demonstrate that the pot residue from the distillation retains catalytically active compounds (e.g., carbamatosilanes) which can be used to react additional quantities of methanol and TRIS. It also indicates that the process of this invention may be operated continuously.

TABLE 5

VAPOR PHASE METHANOLYSIS WITH RECYCLED DISTILLATION RESIDUE

|  | LIGHTS Area % | TRIM Area % | DMAS Area % | TETM Area % | DAMS Area % | TRIS Area % | HVS Area % |
| --- | --- | --- | --- | --- | --- | --- | --- |
| Aminosilane Starting Material | 0.1 | 0.1 | 1.84 | tr | 14.5 | 79.9 | 1.2 |
| Methanolysis Product | 2.4 | 31.7 | 40.7 | 0.4 | 20.6 | 2.5 | 1.7 |

Lights = See Table 1
HVS = See Table 1

TABLE 6

COMPOSITION OF DISTILLATES FROM FIRST RECYCLE EXPERIMENT

| Fraction Number | Pot Temp °C. | Head Temp °C. | Wt. gm | LIGHTS Area % | TRIM Area % | DMAS Area % | TETM Area % | DAMS Area % | TRIS Area % | HVS Area % |
| --- | --- | --- | --- | --- | --- | --- | --- | --- | --- | --- |
| 1 | 120 | 82 | 17 | 4.4 | 93.4 | 0.3 | tr | — | — | 1.8 |
| 2 | 125 | 82–85 | 175 | 1.7 | 97.2 | 0.1 | tr | — | — | 1.0 |
| 3 | 130 | 85 | 206 | 0.8 | 98.5 | tr | ND | — | — | 0.7 |
| 4 | 130 | 85 | 180 | 0.5 | 98.9 | — | — | — | — | 0.5 |
| 5 | 135 | 89 | 188 | 0.6 | 95.9 | 3.1 | ND | tr | — | 0.4 |
| 6 | 142 | 90 | 134 | 0.8 | 91.8 | 6.8 | 0.1 | 0.2 | — | 0.3 |
| Pot Residue |  |  | 770 | 1.0 | 0.4 | 6.8 | 0.5 | 40.4 | 46.9 | 4.2 |

Notes:
LIGHTS = See Table 4.
HVS = See Table 4.

TABLE 7

SECOND RECYCLE OF DISTILLATION RESIDUE TO VAPOR PHASE METHANOLYSIS

|  | LIGHTS Area % | TRIM Area % | DMAS Area % | TETM Area % | DAMS Area % | TRIS Area % | HVS Area % |
| --- | --- | --- | --- | --- | --- | --- | --- |
| Aminosilane Starting Material | 0.3 | 0.2 | 2.5 | 0.2 | 15.1 | 79.5 | 2.2 |
| Methanolysis Product | 3.6 | 31.8 | 39.1 | 1.0 | 18.6 | 1.7 | 2.5 |

Lights = See Table 1
HVS = See Table 1

TABLE 8

COMPOSITION OF DISTILLATES FROM SECOND RECYCLE EXPERIMENT

| Fraction Number | Pot Temp °C. | head Temp °C. | Wt. gm | LIGHTS Area % | TRIM Area % | DMAS Area % | TETM Area % | DAMS Area % | TRIS Area % | HVS Area % |
| --- | --- | --- | --- | --- | --- | --- | --- | --- | --- | --- |
| 1 | 125 | 84 | 408 | 1.9 | 96.9 | 0.2 | tr | ND | — | 0.8 |
| 2 | 125 | 85 | 333 | 1.0 | 97.8 | 0.8 | tr | — | — | 0.4 |
| 3 | 130 | 88 | 47 | 1.1 | 93.4 | 5.1 | 0.1 | — | — | 0.3 |

TABLE 8-continued

| | | COMPOSITION OF DISTILLATES FROM SECOND RECYCLE EXPERIMENT | | | | | | | |
|---|---|---|---|---|---|---|---|---|---|
| Fraction Number | Pot Temp °C. | head Temp °C. | Wt. gm | LIGHTS Area % | TRIM Area % | DMAS Area % | TETM Area % | DAMS Area % | TRIS Area % | HVS Area % |
| Pot Residue | | | 687 | 2.4 | 0.7 | 8.3 | 1.5 | 37.3 | 36.9 | 8.4 |

Notes:
LIGHTS = See Table 4.
HVS = See Table 4.

TABLE 9

| THIRD RECYCLE OF DISTILLATION RESIDUE TO VAPOR PHASE METHANOLYSIS | | | | | | | |
|---|---|---|---|---|---|---|---|
| | LIGHTS Area % | TRIM Area % | DMAS Area % | TETM Area % | DAMS Area % | TRIS Area % | HVS Area % |
| Aminosilane Starting Material | 0.3 | 0.2 | 2.4 | 0.5 | 12.0 | 80.6 | 2.9 |
| Methanolysis Product | 0.7 | 47.1 | 21.5 | 1.1 | 4.3 | 20.3 | 4.5 |

Lights = See Table 1
HVS = See Table 2

TABLE 10

| | | COMPOSITION OF DISTILLATES FROM THIRD RECYCLE EXPERIMENT | | | | | | | |
|---|---|---|---|---|---|---|---|---|---|
| Fraction Number | Pot Temp °C. | Head Temp °C. | Wt. gm | LIGHTS Area % | TRIM Area % | DMAS Area % | TETM Area % | DAMS Area % | TRIS Area % | HVS Area % |
| 1 | 120 | 84 | 435 | 3.6 | 95.3 | 0.1 | — | — | — | 1.0 |
| 2 | 125 | 85 | 227 | 1.2 | 95.4 | 3.0 | — | — | — | 0.3 |
| 3 | 130 | 86 | 45 | 1.8 | 92.3 | 5.3 | 0.1 | 0.1 | — | 0.4 |
| Pot Residue | | | 780 | 0.8 | 1.1 | 8.4 | 3.6 | 37.2 | 33.1 | 11.6 |

Notes:
LIGHTS = See Table 4.
HVS = See Table 4.

EXAMPLE 6

This example illustrates the vapor phase synthesis of triethoxysilane from ethanol and tris(dimethylamino)silane. The catalyst ($CO_2$) level was varied during the experiment in order to determine the catalyst concentrations at which the formation of tetraethoxysilane is minimized.

The conditions used were those described in Example 1, except that the ethanol flow rate was 483 gm/min and the tris(dimethylamino)silane flow rate was 6.27 gm/min. The molar ratio of ethanol to SiN bonds was 0.90. $CO_2$ flow rates were varied between 11–26 cc/min to obtain catalyst concentrations of 0.39–0.90 mole % based on SiN bonds. The experimental data are set forth in Table 11.

The data show that catalyst levels as low as 0.66 mole % (based on the SiN bonds) may be used in the vapor phase synthesis of triethoxysilane while still suppressing tetraethoxysilane formation to less than 0.5% of the crude product.

TABLE 11

| EFFECT OF $CO_2$ CATALYST CONCENTRATION ON THE VAPOR PHASE SYNTHESIS OF TRIETHOXYSILANE | | | | | | | | | | |
|---|---|---|---|---|---|---|---|---|---|---|
| Time (min) | $CO_2$ cm/min | Mole % Catalyst | $CO_2$ Area % | LIGHTS Area % | TRIE Area % | DEAS Area % | DAES Area % | TRIS Area % | TETE Area % | HVS Area % |
| 0 | 26 | 0.92 | | | | | | | | |
| 59 | 26 | 0.92 | 0.9 | 3.4 | 83.3 | 3.2 | 0.7 | 7.2 | 0.3 | 0.9 |
| 89 | 26 | 0.92 | 0.6 | 3.2 | 84.1 | 4.3 | 0.8 | 5.7 | 0.3 | 1.0 |
| 91 | 18.5 | 0.66 | | | | | | | | |
| 146 | 18.5 | 0.66 | 0.6 | 2.9 | 86.2 | 4.1 | 0.7 | 3.9 | 0.4 | 1.1 |
| 175 | 18.5 | 0.66 | 0.4 | 2.9 | 86.1 | 4.8 | 0.7 | 3.6 | 0.4 | 1.1 |
| 201 | 18.5 | 0.66 | 0.4 | 2.5 | 84.9 | 4.7 | 0.8 | 5.0 | 0.3 | 1.2 |
| 204 | 26 | 0.92 | | | | | | | | |
| 253 | 26 | 0.92 | 0.4 | 2.7 | 84.1 | 8.1 | 1.0 | 2.1 | 0.3 | 1.2 |
| 283 | 26 | 0.92 | 0.7 | 3.0 | 81.8 | 10.3 | 1.1 | 1.4 | 0.3 | 1.3 |
| 293 | 11 | 0.39 | | | | | | | | |
| 333 | 11 | 0.39 | 0.2 | 7.0 | 70.8 | 3.1 | 0.4 | 9.4 | 7.8 | 1.2 |
| 359 | 11 | 0.39 | 0.2 | 6.9 | 70.3 | 3.1 | 0.4 | 9.2 | 8.3 | 1.5 |

Note:
LIGHTS = Mostly $HN(CH_3)_2$ plus $H_2NCH_3$ and traces of ethanol.
HVS = $H(CH_3CH_2O)_2SiOSi(OCH_2CH_3)_2H$, $H(CH_3CH_2O)_2SiOSi(OCH_2CH_3)_3$, $(CH_3CH_2O)_3SiOSi(OCH_2CH_3)_3$, $HSi[OOCN(CH_3)_2]_x[N(CH_3)_2]_{3-x}$ (x = 1,2,3), $HSi[OOCN(CH_3)_2]_x(OCH_2CH_3)_{3-x}$ (x = 1,2,3), $CH_3CH_2OSi[OOCN(CH_2CH_3)_2]_x(OCH_3)_{3-x}$ (x = 1,2,3), $CH_3CH_2OSi[N(CH_3)_2]_x[OCH_2CH_3]_{3-x}$ (x = 1,2,3) and $CH_3CH_2OSi[OOCN(CH_3)_2]_x[N(CH_3)_2]_{3-x}$ (x = 1,2,3).

EXAMPLES 7

In this example the vapor phase synthesis of triethoxysilane was conducted at close to an ethanol/SiN bonds molar ratio of 1.0 (range 0.99–1.04) in order to determine the effect of stoichiometry on the formation of tetraethoxysilane.

The procedure described in Example 1 was used except that the ethanol flow rate was varied from 4.63–4.87 gm/min, the flow rate of tris(dimethylamino)silane was 5.48 gm/min and DICARB was used as the catalyst. DICARB was added to the ethanol such that its concentration in ethanol was 7.22 wt. % and its concentration relative to SiN bonds in the vapor phase reactor was approximately 2.5 mole %. The results of Example 6 show this catalyst level to be well above that required to keep tetraethoxysilane formation below 0.5% at an ethanol/SiN stoichiometry of 0.9.

The experimental results are set forth in Table 12. It was observed that total conversion of tris(dimethylamino)silane occurred in the stoichiometry range (0.99–1.04) studied and that the formation of tetraethoxysilane was generally greater than 0.5% under these conditions. Tetraethoxysilane formation was higher at stoichiometries greater than 1.00 than at those below 1.00. From these results the maximum molar ratio of ethanol to SiN bonds for the practice of this invention is set at 0.95. Operation at high stoichiometry advantageously reduces the formation of diethoxydimethylaminosilane, $HSi(OC_2H_5)_2[N(CH_3)_2]$, which has a boiling point (138° C.) quite close to triethoxysilane, $HSi(OC_2H_5)_3$ (132° C.) and can make the recovery of $HSi(OC_2H_5)_3$ by distillation more difficult.

magnetic stir bar and stirrer were also provided. A water cooled condenser with magnetically controlled reflux system was affixed atop the Oldershaw column. In ambient pressure distillations, distillate from the condenser was collected in simple receiving flasks. For distillation under reduced pressure, the simple receiving flask was replaced by a vacuum distillation receiver. This is a reservoir with a double oblique bore stopcock at its outlet to enable drainage of its contents into a simple receiving flask without disturbing the vacuum system.

2248 gm crude triethoxysilane prepared by the method of Example 7 was charged to the distilling flask and a vacuum of 100 mm Hg applied to strip the dissolved $(CH_3)_2NH$ from the product. With the system still at reduced pressure, 120 ml ethanol was added to convert the $HSi(OC_2H_5)_2[N(CH_3)_2]$ in the crude product to $HSi(OC_2H_5)_3$. The ethanol was previously placed in an addition funnel which had a pressure equalizing line. The addition funnel occupied the neck previously closed by the ground-glass stopper. Addition of the ethanol was made slowly over a two hour period with

TABLE 12

EFFECT OF ETHANOL/SiN STOICHIOMETRY ON THE VAPOR PHASE SYNTHESIS OF TRIETHOXYSILANE

| Time (min) | Ethanol gm/min | RATIO Ethanol SiN | $CO_2$ Area % | LIGHTS Area % | TRIE Area % | DEAS Area % | DAES Area % | TETE Area % | HVS Area % |
|---|---|---|---|---|---|---|---|---|---|
| 0 | 4.63 | 0.99 | | | | | | | |
| 60 | 4.63 | 0.99 | 1.2 | 3.2 | 82.5 | 9.0 | 0.7 | 0.5 | 0.5 |
| 64 | 4.67 | 1.00 | | | | | | | |
| 91 | 4.67 | 1.00 | 1.2 | 3.2 | 80.7 | 11.0 | 0.8 | 0.1 | 0.5 |
| 100 | 4.71 | 1.00 | | | | | | | |
| 125 | 4.71 | 1.00 | 0.6 | 4.2 | 89.1 | 2.5 | — | 0.5 | 0.7 |
| 135 | 4.75 | 1.01 | | | | | | | |
| 166 | 4.75 | 1.01 | 0.8 | 4.0 | 88.5 | 2.4 | — | 0.8 | 1.2 |
| 169 | 4.79 | 1.02 | | | | | | | |
| 200 | 4.79 | 1.02 | 0.4 | 4.2 | 88.4 | 3.5 | 0.1 | 0.7 | 0.7 |
| 211 | 4.83 | 1.03 | | | | | | | |
| 238 | 4.83 | 1.03 | 0.8 | 4.4 | 86.7 | 4.2 | 0.1 | 0.7 | 0.5 |
| 267 | 4.83 | 1.03 | 1.4 | 7.6 | 83.0 | 0.7 | — | 4.4 | 2.0 |
| 275 | 4.87 | 1.04 | | | | | | | |
| 312 | 4.87 | 1.04 | 0.2 | 5.1 | 87.7 | 2.8 | — | 1.1 | 1.3 |
| 318 | 4.83 | 1.03 | | | | | | | |
| 355 | 4.83 | 1.03 | 1.0 | 5.1 | 87.9 | 2.1 | — | 0.8 | 0.9 |
| 388 | 4.83 | 1.03 | 1.0 | 3.7 | 84.7 | 6.9 | 0.2 | 0.8 | 0.6 |

Note:
LIGHTS = Mostly $HN(CH_3)_2$ plus $H_2NCH_3$ and traces of ethanol.
HVS = See Table 11.

EXAMPLE 8

This example illustrates the recovery of triethoxysilane by distillation of the crude ethanolysis product.

The distillation apparatus consisted of a 3000 ml round bottom 3-neck flask attached to a 30 plate Oldershaw column. To the remaining two necks were attached a thermometer and ground-glass stopper, respectively. The flask was heated with a heating mantle. A vigorous stirring of the flask's contents. When the ethanol addition was completed, the vacuum was released and the contents of the flask were sampled for GC analysis. The flask was again evacuated to 100 mm Hg and then heated slowly to 79° C. Distillation fractions were collected at the head temperatures and reflux ratios shown in Table 13. A total of 1959 gm $HSi(OC_2H_5)_3$ was recovered.

TABLE 13

RECOVERY OF TRIETHOXYSILANE BY DISTILLATION IN VACUO (100 mm Hg)

| | Pot Temp °C. | Head Temp °C. | Reflux Ratio | Wt. gm | LIGHTS Area % | TRIE Area % | DEAS Area % | TETE Area % | DAES Area % | TRIS Area % | HVS Area % |
|---|---|---|---|---|---|---|---|---|---|---|---|
| Starting Material | | | | 2248 | 4.7 | 75.0 | 16.0 | 0.4 | 1.7 | tr | 2.1 |
| After Ethanol Fractions | | | | | 4.2 | 90.5 | 1.6 | 0.7 | tr | tr | 2.9 |
| 1 | 79 | 68 | 1 | 28 | 19.9 | 74.5 | 4.6 | 0.5 | tr | tr | 0.5 |
| 2 | 80 | 70 | 1 | 314 | 3.0 | 96.8 | 0.1 | — | — | — | tr |
| 3 | 80 | 69 | 1 | 381 | 0.9 | 98.6 | 0.4 | — | — | — | tr |
| 4 | 82 | 72 | 1 | 369 | 0.3 | 98.6 | 1.0 | — | — | — | 0.1 |
| 5 | 86 | 74 | 1 | 360 | 0.1 | 97.8 | 1.9 | — | — | — | 0.1 |
| 6 | 96 | 74 | 2 | 351 | tr | 96.1 | 3.5 | — | 0.1 | — | 0.1 |
| 7 | 160 | 75 | 4 | 245 | 1.5 | 82.7 | 13.8 | 0.1 | 1.3 | — | 0.2 |

TABLE 13-continued

| | RECOVERY OF TRIETHOXYSILANE BY DISTILLATION IN VACUO (100 mm Hg) | | | | | | | | | |
|---|---|---|---|---|---|---|---|---|---|---|
| | Pot Temp °C. | Head Temp °C. | Reflux Ratio | Wt. gm | LIGHTS Area % | TRIE Area % | DEAS Area % | TETE Area % | DAES Area % | TRIS Area % | HVS Area % |
| 8 | 178 | 78 | 4 | 15 | 16.4 | 21.6 | 27.9 | 7.9 | 17.1 | 6.8 | 1.9 |
| Pot Residue | | | | 75 | 3.2 | 2.8 | 3.0 | 30.4 | 2.5 | 0.8 | 57.3 |

Notes:
LIGHTS = See Table 11.
HVS = See Table 11.

EXAMPLE 9

This example illustrates the recovery of the higher boiling fraction (>132° C.) from the vapor phase ethanolysis of tris(dimethylamino)silane and its recycle to the vapor phase reactor for the synthesis of additional triethoxysilane. Each recycle experiment consists of a vapor phase ethanolysis followed by a distillation of triethoxysilane from the crude ethanolysis product.

9A Vapor Phase Reaction

The vapor phase ethanolysis was performed as described in Example 7, using a DICARB concentration of 4.22 mole % relative to the SiN bonds, a TRIS flow rate of 6.27 gm/min and an average ethanol flow rate of 3.59 gm/min. The reaction temperature was 200° C. The weight of crude product was 2118.9 gm.

Distillation 2108 gm of crude triethoxysilane from the vapor phase ethanolysis of Example 9A was distilled at atmospheric pressure using the distillation apparatus described in Example 4. The composition of the crude triethoxysilane is given in the first row of Table 14. Seven distillate fractions were collected. As Table 14 reveals, the separation of HSi(OC$_2$H$_5$)$_2$[N(CH$_3$)$_2$] (bpt 138° C.) from HSi(OC$_2$H$_5$)$_3$ (bpt 132° C.) was not accomplished even though reflux ratios of 20–50 were employed. The pot residue from the distillation weighed 934 gm and gave a CO$_2$ peak area of 5% by GC.

9B Vapor Phase Reaction 1161 gms TRIS were mixed with the 934 gm pot residue from the distillation of Example 9A and reacted with ethanol in the method of Example 9A. No additional catalyst was added. The aminosilane flow rate was 6.27 gm/min and the average ethanol flow rate 3.48 gm/min. 1156 gm ethanol and 2083 gm aminosilane were consumed. The crude product weighed 2069 gm and had the composition shown in the first row of Table 15.

Distillation 2018 gm of the vapor phase reaction product from Example 9B was stripped of dissolved dimethylamine at room temperature and 100 mm Hg. The liquid residue (second row of Table 15) was then treated with 66 ml ethanol to convert the contained HSi(OC$_2$H$_5$)$_2$[N(CH$_3$)$_2$] to HSi(OC$_2$H$_5$)$_3$. The pot temperature was raised to 136° C. following the ethanol addition. The initial distillate (#1 of Table 15) was high in HVS, primarily dimethylcarbamatotriethoxysilane, because there was virtually no unreacted TRIS left in the vapor phase reaction product. Distillation of the mixture was performed at atmospheric pressure. Fractions were collected at the head temperatures shown in Table 15 and at reflux ratios of 2–4. It is seen that the purity of the distilled triethoxysilane was significantly better than that shown in Table 14.

SUMMARY OF RECYCLE EXPERIMENTS

The data of this example confirm that the pot residue from the distillation of the vapor phase ethanolysis product retains catalytically active compounds (e.g., carbamatosilanes) which are recyclable to the vapor phase ethanolysis. It is also demonstrated that the distillation is most efficiently performed with little or no HSi(OC$_2$H$_5$)$_2$[N(CH$_3$)$_2$] in the crude product. After two vapor phase reaction/distillation cycles the Si(OC$_2$H$_5$)$_4$ content was 2.5% (i.e., 1.25% per cycle).

TABLE 14

| COMPOSITION OF THE DISTILLATES FROM DISTILLATION OF CRUDE TRIETHOXYSILANE AT 1 ATMOSPHERE | | | | | | | | | | |
|---|---|---|---|---|---|---|---|---|---|---|
| | Pot Temp, °C. | Head Temp, °C. | Wt. gm | LIGHTS Area % | TRIE Area % | DEAS Area % | DAES Area % | TRIS Area % | TETE Area % | HVS Area % |
| Starting Material | | | 2108 | 1.9 | 50.9 | 13.7 | 3.2 | 26.7 | 0.4 | 1.4 |
| 1 | 142 | 126 | 50 | 30.8 | 57.3 | 10.5 | 0.8 | 0.4 | ND | ND |
| 2 | 144 | 134 | 252 | 3.8 | 56.3 | 29.2 | 9.7 | 1.1 | ND | ND |
| 3 | 146 | 135 | 283 | 1.5 | 50.3 | 33.3 | 14.0 | 1.0 | ND | 0.1 |
| 4 | 148 | 136 | 243 | 0.6 | 43.0 | 36.2 | 18.9 | 1.1 | ND | 0.1 |
| 5 | 151 | 136 | 252 | 1.1 | 40.1 | 37.0 | 20.5 | 1.2 | ND | 0.1 |
| 6 | 151 | 132 | 43 | 4.1 | 38.0 | 36.8 | 19.9 | 1.2 | ND | ND |
| 7 | 151 | 132 | 19 | 18.1 | 49.6 | 25.6 | 5.9 | 0.6 | tr | 0.1 |
| Pot Residue | | | 934 | 0.4 | 7.0 | 23.5 | 38.4 | 17.1 | 2.8 | 5.8 |

LIGHTS = See Table 11
HVS = See Table 11

TABLE 15

| COMPOSITION OF THE DISTILLATES FROM VAPOR PHASE ETHANOLYSIS WITH RECYCLED CATALYST | | | | | | | | | |
|---|---|---|---|---|---|---|---|---|---|
| | Pot Temp, °C. | Head Temp, °C. | Wt. gm | LIGHTS Area % | TRIE Area % | DEAS Area % | DAES Area % | TRIS Area % | TETE Area % | HVS Area % |
| Starting Material | | | 2018 | 3.1 | 78.6 | 10.4 | 0.6 | tr | 2.5 | 3.3 |
| After DMA Stripping | | | | 6.5 | 82.2 | 2.7 | tr | 0.1 | 3.7 | 4.1 |
| 1 | 136 | 136 | 71 | 13.6 | 8.8 | 5.8 | 1.2 | 0.2 | 25.7 | 34.4 |
| 2 | 126 | 130 | 154 | 5.7 | 93.9 | tr | ND | tr | tr | 0.2 |

TABLE 15-continued
COMPOSITION OF THE DISTILLATES FROM VAPOR PHASE ETHANOLYSIS WITH RECYCLED CATALYST

| | Pot Temp, °C. | Head Temp, °C. | Wt. gm | LIGHTS Area % | TRIE Area % | DEAS Area % | DAES Area % | TRIS Area % | TETE Area % | HVS Area % |
|---|---|---|---|---|---|---|---|---|---|---|
| 3 | 138 | 132 | 316 | 2.5 | 96.9 | 0.1 | ND | 0.1 | ND | 0. |
| 4 | 140 | 132 | 364 | 1.5 | 96.8 | 1.0 | ND | tr | ND | 0. |
| 5 | 144 | 132 | 335 | 1.4 | 95.3 | 2.1 | tr | 0.1 | ND | 0.7 |
| 6 | 157 | 132 | 337 | 1.2 | 91.2 | 6.6 | 0.2 | 0.1 | ND | 0.4 |
| 7 | 176 | 137 | 163 | 3.6 | 81.4 | 12.6 | 1.0 | 0.1 | 0.2 | 0.2 |
| 8 | 180 | 151 | 32 | 8.6 | 41.5 | 17.1 | 2.8 | 1.0 | 22.5 | 0.4 |
| Pot Residue | | | 207 | 0.4 | 1.6 | 1.3 | 0.7 | 0.1 | 57.0 | 36.6 |

LIGHTS = See Table 11
HVS = See Table 11

EXAMPLES 10

This example illustrates the vapor phase synthesis of tri-isopropoxysilane from isopropanol and tris(dimethylamino)silane.

The procedure used was that of Example 1, except that the isopropanol flow was varied in the range 4.78–6.66 gm/min; the tris(dimethylamino)silane flow was 7.77 gm/min. The catalyst ($CO_2$) concentration was varied as shown in Table 16 from 1.71–2.90 mole % based on the SiN bonds. The vapor phase reaction produced a total of 1821 gm of crude tri-isopropoxysilane during 214 minutes of reaction. The gc separation of TRIS from the mixed dimethylamino-isopropoxysilanes, i.e., $HSi[N(CH_3)_2]_x[OCH(CH_3)_2]_{3-x}$ (x=1 or 2,) is difficult. Consequently, the column entitled TRIS in Table 16 is the combined area percent of all three compounds.

The procedure used was that of Example 1 except as noted hereinbelow. The vapor phase reactor was operated at 250° C. and the tris(dimethylamino)silane vaporizer also at 250° C. The flow rate of tris(dimethylamino)silane was 10.70 gm/min and the catalyst concentration (85 cc/min $CO_2$) was equal to 1.77 mole % of the SiN bonds. Tert butanol was introduced at flow rates in the range 10.70–15.65 gm/min, thus giving stoichiometries of alcohol to SiN of 0.72–1.06.

The results of this vapor phase synthesis are set forth in Table 17. A total of 3134.5 gm crude tri(tert-butoxy)silane was obtained from the 2244 gm tert-butanol and 1840 gm tris(dimethylamino)silane fed to the reactor. Table 17 shows that when the alcohol is sterically hindered, such as tert-butanol the reaction can readily be run at high t-butanol/SiN stoichiometries, i.e., 0.88–1.00 without producing tetra(tert butoxy)silane. Indeed, excess tert-butanol persisted at t-butanol/SiN stoichi-

TABLE 16
VAPOR PHASE SYNTHESIS OF TRI-ISOPROPOXYSILANE

| $CO_2$ cc/min | Mole % Catalyst | Iso-propanol gm/min | Iso-propanol SiN | $CO_2$ Area % | LIGHTS Area % | TRIS Area % | TRIP Area % | HVS Area % |
|---|---|---|---|---|---|---|---|---|
| 60 | 1.71 | 4.78 | 0.55 | 0.5 | 2.3 | 36.0 | 59.6 | 1.5 |
| 70 | 2.00 | 5.25 | 0.60 | 0.6 | 2.7 | 28.6 | 64.8 | 3.2 |
| 80 | 2.28 | 5.72 | 0.66 | 0.7 | 3.2 | 16.6 | 75.4 | 4.0 |
| 90 | 2.56 | 6.19 | 0.71 | 2.4 | 2.7 | 17.7 | 76.3 | 0.9 |
| 90 | 2.56 | 6.19 | 0.71 | 1.8 | 1.9 | 15.3 | 79.8 | 1.2 |
| 102 | 2.90 | 6.66 | 0.77 | 2.6 | 2.7 | 7.84 | 85.6 | 1.0 |

Note:
LIGHTS = Mainly $HN(CH_3)_2$ plus $H_2NCH_3$
HVS = $HSi[OCH(CH_3)_2]_x[OOCN(CH_3)_2]_{3-x}$ (x = 1, 2), $HSi[OOCN(CH_3)_2]_x[N(CH_3)_2]_{3-x}$ (x = 1, 2, 3), $H_xSi_2O[OCH(CH_3)_2]_{6-x}$ (x = 0, 1, 2).

ometries greater than 1.00.

TABLE 17
VAPOR PHASE SYNTHESIS OF TRI-(TERT-BUTOXY)SILANE

| Tert-Butanol gm/min | t-Butanol SiN | $CO_2$ Area % | LIGHTS Area % | t-Butanol Area % | TRIS Area % | DBAS Area % | TTBS Area % | HVS Area % |
|---|---|---|---|---|---|---|---|---|
| 10.70 | 0.72 | 1.04 | 19.34 | — | 2.03 | 44.10 | 32.56 | 0.94 |
| 10.70 | 0.72 | 0.99 | 18.18 | — | 2.43 | 46.76 | 30.51 | 1.14 |
| 11.71 | 0.79 | 0.99 | 23.10 | — | 0.16 | 32.43 | 42.51 | 1.08 |
| 11.71 | 0.79 | 0.92 | 22.54 | — | 0.03 | 29.94 | 42.95 | 3.62 |
| 13.05 | 0.88 | 0.65 | 22.66 | — | 0.03 | 18.05 | 55.67 | 2.94 |
| 13.05 | 0.88 | 1.67 | 21.86 | — | — | 15.69 | 54.11 | 6.69 |
| 14.24 | 0.96 | 1.58 | 25.61 | — | 0.04 | 1.30 | 69.08 | 2.87 |
| 14.24 | 0.96 | 1.87 | 22.55 | — | — | 0.93 | 70.83 | 3.82 |
| 15.65 | 1.06 | 1.76 | 22.68 | 5.89 | — | 0.92 | 67.23 | 1.85 |
| 15.65 | 1.06 | 1.76 | 25.98 | 5.17 | — | 0.90 | 65.03 | 1.37 |

Note:
LIGHTS = Mostly $(CH_3)_2NH$ and $H_2NCH_3$.
HVS = $H(OH_9C_4\text{-}t)_2SiOSi(OH_9C_4\text{-}t)_2H$, $HSi[OOCN(CH_3)_2]_x[N(CH_3)_2]_{3-x}$ (x = 1, 2, 3), $HSi[OOCN(CH_3)_2]_x[OH_9C_4\text{-}t]_{3-x}$ (x = 1, 2, 3)

EXAMPLE 11

This example illustrates the vapor phase synthesis of tri(tert butoxy)silane from tris(dimethylamino)silane and tert butanol.

That which is claimed is:

1. A vapor phase process for the synthesis of alkoxysilanes of the general formula $HSi(OR''')_x(R'')_{3-x}$ wherein $R''$, $R'''$ and X are as defined below, which comprises reacting
   (a) an aminosilane of the general formula $HSi(NRR')_x(R'')_{3-x}$ wherein R and R' are individually hydrogen or a substituted or unsubstituted aryl, alkenyl or alkyl group, each having from one to eight carbon atoms inclusive, and where $R''$ is $R'$ or an alkoxy or carbamato group and where x has a value of from one to three; with
   (b) an alcohol of the general formula $R'''OH$ wherein $R'''$ is a substituted or unsubstituted aryl, alkenyl group or alkyl group, each having from one to twenty carbon atoms inclusive, said reaction taking place in the presence of
   (c) a catalyst in which both the aminosilane and the alcohol are present in gaseous form in a stoichiometric ratio of 0.4 to 1.05 moles of alcohol per mole of silicon-nitrogen bonds in the aminosilane and where said catalyst is present in an amount from 0.01 to 10 mole percent of the silicon-nitrogen bonds of the aminosilane.

2. The process of claim 1 wherein R, R' and $R''$ of the aminosilane and $R'''$ of the alcohol are independently alkyl groups having one to six carbon atoms inclusive.

3. The process of claim 1 wherein x is three.

4. The process of claim 1 wherein the reaction temperature is at least 5° C. greater than the boiling point of the highest boiling component of the reaction mixture determined under reaction zone conditions.

5. The process of claim 1 wherein the alcohol is methanol.

6. The process of claim 5 wherein the catalyst concentration is between 2.0 and 6.0 mole percent of the silicon-nitrogen bonds in the aminosilane and the molar ratio of methanol to silicon-nitrogen bonds is 0.45 to 0.95.

7. The process of claim 5 wherein the catalyst concentration is between 3.5 and 5.0 mole percent of the silicon-nitrogen bonds in the aminosilane and the molar ratio of methanol to silicon-nitrogen bonds is 0.55 to 0.85.

8. The process of claim 1 wherein the alcohol is selected from the group consisting of ethanol, n-propanol and isopropanol.

9. The process of claim 8 wherein the catalyst concentration is between 2.0 and 6.0 mole percent of the silicon-nitrogen bonds in the aminosilane and the molar ratio of alcohol to silicon-nitrogen bonds is 0.65 to 0.95.

10. The process of claim 8 wherein the catalyst concentration is between 3.5 and 5.0 mole percent of the silicon-nitrogen bonds in the aminosilane and the molar ratio of alcohol to silicon-nitrogen bonds is 0.75 to 0.95.

11. The process of claim 1 wherein the alcohol is t-butanol the catalyst concentration is between 2.0 and 6.0 mol percent of the silicon-nitrogen bonds in the aminosilane and the molar ratio of alcohol to silicon-nitrogen bonds is 0.80 to 1.05

12. The process of claim 1 wherein the catalyst is carbon dioxide.

13. A vapor phase process for the synthesis of alkoxysilanes of the general formula $HSi(OR''')_x(R'')_{3-x}$ wherein $R''$, $R'''$ and x are as defined below which comprises reacting
   (a) an aminosilane of the general formula $HSi(NRR')_x(R'')_{3-x}$ with (b) an alcohol of the general formula $R'''OH$ wherein R, R', and $R'''$ are independently hydrogen, or alkyl groups having one to six carbon atoms inclusive, $R''$ is $R'$ or an alkoxy or carbamato group, x has a value of from one to three, in the presence of
   (c) a catalyst in which both the aminosilane and the alcohol are present in gaseous form in a stoichiometric ratio of 0.5 to 1.05 moles of alcohol per mole of silicon-nitrogen bonds of the aminosilane and where the catalyst concentration is from 0.01 to 10 mole percent of the silicon-nitrogen bonds.

14. The process of claim 13 wherein the alcohol is methanol.

15. The process of claim 13 wherein the alcohol is ethanol.

16. The process of claim 13 wherein the alcohol is 2-methoxyethanol.

17. The process of claim 13 wherein R, R' and $R''$ of the aminosilane are each methyl groups.

18. The process of claim 17 wherein x is equal to 3.

19. The process of claim 13 wherein the reaction temperature is at least 5° C. greater than the boiling point of the highest boiling alkoxysilane determined under reaction zone conditions.

20. The process of claim 13 wherein the alcohol is methanol, the catalyst concentration is between 2.0 and 6.0 mole percent of the silicon-nitrogen bonds of the aminosilane and the molar ratio of methanol to silicon-nitrogen bonds is 0.45 to 0.95.

21. The process of claim 13 wherein the alcohol is methanol, the catalyst concentration is between 3.5 and 5.0 mole percent of the silicon-nitrogen bonds of the aminosilane, and the molar ratio of methanol to silicon-nitrogen bonds is 0.55 to 0.85.

22. The process of claim 13 wherein the alcohol is ethanol, the catalyst concentration is between 2.0 and 6.0 mole percent of the silicon-nitrogen bonds of the aminosilane and the molar ratio of ethanol to silicon-nitrogen bonds is 0.65 to 0.95.

23. The process of claim 13 wherein the alcohol is ethanol, the catalyst concentration is between 3.5 and 5.0 mole percent of the silicon-nitrogen bonds of the aminosilane, and the molar ratio of ethanol to silicon-nitrogen bonds is 0.75 to 0.95.

24. The process of claim 13 wherein the silane is tris(dimethylamino)silane, the alcohol is selected from the group consisting of methanol, ethanol and 2-methoxyethanol, the temperature is at least 5° C. greater than the boiling point of the highest boiling alkoxysilane determined under reaction zone conditions, the catalyst is dimethylammonium dimethylcarbamate, the catalyst concentration is between 3.5 and 5.0 mole percent of the silicon-nitrogen bonds and the molar ratio of alcohol to silicon-nitrogen bonds is 0.45 to 0.95.

25. The process of claim 13 wherein the catalyst is carbon dioxide.

26. The process of claim 1 wherein the desired alkoxysilane product is recovered and the mixture of by-products is recycled to the vapor phase.

* * * * *

UNITED STATES PATENT AND TRADEMARK OFFICE
CERTIFICATE OF CORRECTION

PATENT NO. : 4,730,074

DATED : March 8, 1988

INVENTOR(S) : Kenrick M. Lewis, Frank D. Mendecino, Nan S. Chu

It is certified that error appears in the above-identified patent and that said Letters Patent is hereby corrected as shown below:

Cover page, second column of the Abstract, 4th line after the formula: " R' " should read --- R" ---.

Column 5, the compounds on line 65 should read: --- 3-ethylhexan-1-ol, 3-ethylhexan-2-ol ---.

Column 5, the compound on line 68 should read: --- 2-dimethylaminopropan-1-ol ---.

Column 6, the compounds on lines 1 and 2 should read: --- 2-methyl-3-butyne-2-ol, 3-methyl-1-pentyne-3-ol ---.

Columns 13 and 14, in the first line of the Note following the table: " $H_2NDH_3$ " should read --- $H_2NCH_3$ ---.

Column 13, line 45: " 613 " should read --- 6.13 ---.

Column 14, Table 3, 2nd column from right, 3rd line down: " 24.8 " should read --- 34.8 ---.

Column 19, line 62: " 483 " should read --- 4.83 ---.

Column 22, line 1: " maqnetic " should read --- magnetic ---.

UNITED STATES PATENT AND TRADEMARK OFFICE
CERTIFICATE OF CORRECTION

PATENT NO. : 4,730,074

DATED : March 8, 1988

INVENTOR(S) : Kenrick M. Lewis, Frank D. Mendecino, Nan S. Chu

It is certified that error appears in the above-identified patent and that said Letters Patent is hereby corrected as shown below:

Column 25, line 66: " tri(tert butoxy)silane " should read --- tri(tert-butoxy)silane ---.

Column 25, last line: " tert butanol " should read --- tert-butanol ---.

Column 26, line 20: " Tert butanol " should read --- Tert-butanol ---.

Column 26, line 30: " tetra(tert butoxy)silane " should read --- tetra(tert-butoxy)silane ---.

Column 27, line 3: " X " should read --- x ---.

Signed and Sealed this

Seventeenth Day of January, 1989

Attest:

DONALD J. QUIGG

*Attesting Officer*  *Commissioner of Patents and Trademarks*